US008551067B2

(12) United States Patent  (10) Patent No.: US 8,551,067 B2
Zinger et al.  (45) Date of Patent: Oct. 8, 2013

(54) NEEDLELESS ADDITIVE CONTROL VALVE

(75) Inventors: Freddy Zinger, Ra'anana (IL); Igor Denenburg, Beberi (LV)

(73) Assignee: Medimop Medical Projects Ltd., Ra'anana (IL)

( * ) Notice: Subject to any disclaimer, the term of this patent is extended or adjusted under 35 U.S.C. 154(b) by 292 days.

(21) Appl. No.: 12/112,490

(22) Filed: Apr. 30, 2008

(65) Prior Publication Data

US 2008/0262465 A1  Oct. 23, 2008

Related U.S. Application Data

(63) Continuation-in-part of application No. PCT/IL2006/001228, filed on Oct. 26, 2006.

(30) Foreign Application Priority Data

Oct. 30, 2005 (IL) .......................... 171662

(51) Int. Cl.
A61M 39/22 (2006.01)
A61M 39/00 (2006.01)
A61M 39/14 (2006.01)
A61M 39/16 (2006.01)
A61M 39/26 (2006.01)

(52) U.S. Cl.
USPC ........... 604/411; 604/403; 604/408; 604/412; 604/414; 604/415; 604/416

(58) Field of Classification Search
USPC ......... 604/411, 407, 415, 416, 403, 405, 412, 604/413, 414
See application file for complete search history.

(56) References Cited

U.S. PATENT DOCUMENTS 1,021,681 A 3/1912 Jennings
3,788,524 A 1/1974 Davis et al.
3,822,700 A 7/1974 Pennington
(Continued)

FOREIGN PATENT DOCUMENTS

IL 171662 10/2005
JP 03-062426 B 9/1991
(Continued)

OTHER PUBLICATIONS

International Search Report Issued Jan. 23, 2007 in Int'l Application No. PCT/IL/2006/001228.
(Continued)

Primary Examiner — Adam Marcetich
(74) Attorney, Agent, or Firm — Panitch Schwarze Belisario & Nadel LLP

(57) ABSTRACT

A needleless additive control valve for use with a fluid container containing an infusion liquid and having an intravenous (IV) port for administrating the infusion liquid, and an additive transfer device containing a liquid additive and having a male connector for administrating the liquid additive. The needleless additive control valve includes a trifurcated connector body having an IV spike for sealing insertion into the IV port, an outlet port, and a needleless additive port with a female connector for sealingly receiving the additive transfer device's male connector wherein the IV spike, the outlet port and the needleless additive port are in 3 way direct and continuous fluid communication thereby enabling the additive transfer device's liquid additive to be either mixed with the infusion liquid or directly administered to a patient.

1 Claim, 5 Drawing Sheets

(56) References Cited

U.S. PATENT DOCUMENTS

| | | | | |
|---|---|---|---|---|
| 3,938,520 | A | 2/1976 | Scislowicz et al. | |
| 4,121,585 | A | 10/1978 | Becker, Jr. | |
| 4,161,178 | A | 7/1979 | Genese | |
| 4,203,067 | A | 5/1980 | Fitzky et al. | |
| 4,203,443 | A | 5/1980 | Genese | |
| 4,303,067 | A | 12/1981 | Connolly et al. | |
| 4,335,717 | A | 6/1982 | Bujan et al. | |
| D268,871 | S | 5/1983 | Benham et al. | |
| 4,392,850 | A | 7/1983 | Elias et al. | |
| 4,410,321 | A | 10/1983 | Pearson et al. | |
| 4,411,662 | A | 10/1983 | Pearson | |
| 4,465,471 | A | 8/1984 | Harris et al. | |
| 4,573,993 | A | 3/1986 | Hoag et al. | |
| 4,581,014 | A | 4/1986 | Millerd et al. | |
| 4,752,292 | A | 6/1988 | Lopez et al. | |
| 4,804,366 | A | 2/1989 | Zdeb et al. | |
| 4,832,690 | A | 5/1989 | Kuu | |
| 4,857,062 | A * | 8/1989 | Russell | 604/256 |
| 4,931,040 | A | 6/1990 | Haber et al. | |
| 4,932,944 | A | 6/1990 | Jagger et al. | |
| 5,006,114 | A | 4/1991 | Rogers et al. | |
| 5,125,915 | A | 6/1992 | Berry et al. | |
| D328,788 | S | 8/1992 | Sagae et al. | |
| 5,242,432 | A | 9/1993 | DeFrank | |
| D341,420 | S | 11/1993 | Conn | |
| 5,300,034 | A | 4/1994 | Behnke et al. | |
| 5,445,630 | A * | 8/1995 | Richmond | 604/411 |
| 5,547,471 | A | 8/1996 | Thompson et al. | |
| 5,549,577 | A | 8/1996 | Siegel et al. | |
| 5,603,706 | A * | 2/1997 | Wyatt et al. | 604/539 |
| 5,645,538 | A | 7/1997 | Richmond | |
| 5,647,845 | A | 7/1997 | Haber et al. | |
| 5,651,776 | A | 7/1997 | Appling et al. | |
| 5,676,346 | A | 10/1997 | Leinsing | |
| 5,766,211 | A * | 6/1998 | Wood et al. | 604/32 |
| 5,776,116 | A | 7/1998 | Lopez et al. | |
| 5,782,872 | A * | 7/1998 | Muller | 604/404 |
| 5,853,406 | A | 12/1998 | Masuda et al. | |
| 5,887,633 | A | 3/1999 | Yale et al. | |
| 5,893,397 | A | 4/1999 | Peterson et al. | |
| 5,897,526 | A * | 4/1999 | Vaillancourt | 604/82 |
| 5,911,710 | A * | 6/1999 | Barry et al. | 604/249 |
| 5,935,112 | A * | 8/1999 | Stevens et al. | 604/256 |
| 5,941,848 | A | 8/1999 | Nishimoto et al. | |
| 6,099,511 | A | 8/2000 | Devos et al. | |
| 6,142,446 | A * | 11/2000 | Leinsing | 251/149.1 |
| 6,146,362 | A * | 11/2000 | Turnbull et al. | 604/256 |
| 6,171,287 | B1 * | 1/2001 | Lynn et al. | 604/256 |
| 6,179,822 | B1 * | 1/2001 | Niedospial, Jr. | 604/408 |
| 6,179,823 | B1 * | 1/2001 | Niedospial, Jr. | 604/408 |
| 6,221,065 | B1 * | 4/2001 | Davis | 604/539 |
| 6,290,688 | B1 | 9/2001 | Lopez et al. | |
| 6,296,621 | B1 | 10/2001 | Masuda et al. | |
| 6,358,236 | B1 | 3/2002 | DeFoggi et al. | |
| 6,440,107 | B1 * | 8/2002 | Trombley et al. | 604/256 |
| 6,453,949 | B1 * | 9/2002 | Chau | 138/89 |
| D468,015 | S | 12/2002 | Horppu | |
| 6,571,837 | B2 | 6/2003 | Jansen et al. | |
| D482,121 | S | 11/2003 | Harding et al. | |
| D482,447 | S | 11/2003 | Harding et al. | |
| 6,692,478 | B1 | 2/2004 | Paradis | |
| 6,699,229 | B2 | 3/2004 | Zinger et al. | |
| 6,706,022 | B1 * | 3/2004 | Leinsing et al. | 604/247 |
| 6,875,205 | B2 | 4/2005 | Leinsing | |
| 6,997,916 | B2 | 2/2006 | Simas, Jr. et al. | |
| 7,070,589 | B2 | 7/2006 | Lolachi et al. | |
| 7,192,423 | B2 | 3/2007 | Wong | |
| 7,241,285 | B1 * | 7/2007 | Dikeman | 604/533 |
| 7,326,188 | B1 | 2/2008 | Russell et al. | |
| 7,544,191 | B2 | 6/2009 | Peluso et al. | |
| 8,122,923 | B2 * | 2/2012 | Kraus et al. | 141/329 |
| 2002/0128628 | A1 * | 9/2002 | Fathallah | 604/411 |
| 2003/0028156 | A1 | 2/2003 | Juliar | |
| 2003/0073971 | A1 | 4/2003 | Saker | |
| 2003/0187420 | A1 | 10/2003 | Akerlund et al. | |
| 2003/0191445 | A1 | 10/2003 | Wallen et al. | |
| 2003/0199847 | A1 | 10/2003 | Akerlund et al. | |
| 2004/0073189 | A1 | 4/2004 | Wyatt et al. | |
| 2004/0204699 | A1 | 10/2004 | Hanly et al. | |
| 2005/0015070 | A1 * | 1/2005 | Delnevo et al. | 604/408 |
| 2005/0182383 | A1 | 8/2005 | Wallen | |
| 2006/0095015 | A1 | 5/2006 | Hobbs et al. | |
| 2006/0106360 | A1 * | 5/2006 | Wong | 604/411 |
| 2007/0024995 | A1 | 2/2007 | Hayashi | |
| 2007/0299404 | A1 | 12/2007 | Katoh et al. | |

FOREIGN PATENT DOCUMENTS

| | | | |
|---|---|---|---|
| JP | 06-050656 | U | 7/1994 |
| JP | 2002-035140 | A | 2/2002 |
| JP | 2002-516160 | A | 6/2002 |
| JP | 2002-355318 | A | 12/2002 |
| JP | 2003-033441 | A | 2/2003 |
| WO | 9961093 | A1 | 12/1999 |
| WO | 02089900 | A1 | 11/2002 |
| WO | 03/079956 | A1 | 10/2003 |
| WO | 2005041846 | A2 | 5/2005 |

OTHER PUBLICATIONS

IV disposables sets catalogue, Cardinal Health, Alarisa products, SmartSitea access devices and accessories product No. 10013365, SmartSite add-on bag access device with spike adapter and needle-free valve bag access port, pp. 1-5, Fall edition (2007).

http://www.westpharma.com/eu/en/products/Pages/Vial2Bag.aspx; Drug Adminsitration Systems product information sheets pp. 1-3.

Article with picture of West Pharmaceutical Services'Vial2Bag Needleless System, [on-line]; ISIPS Newsletter, Oct. 26, 2007]; retrieved from Internet Feb. 16, 2010]; URL:<http://www.isips.org/reports/ISIPS_Newsletter_October_26_2007. html.> (7 pages. see pp. 5-6).

Office Action issued Jun. 15, 2011 in JP Application No. 2008-538492.

Translation of Office Action issued Jun. 18, 2012 in JP Application No. 2008-538492.

Translation of Office Action issued Apr. 15, 2013 in JP Application No. 2008-538492.

\* cited by examiner

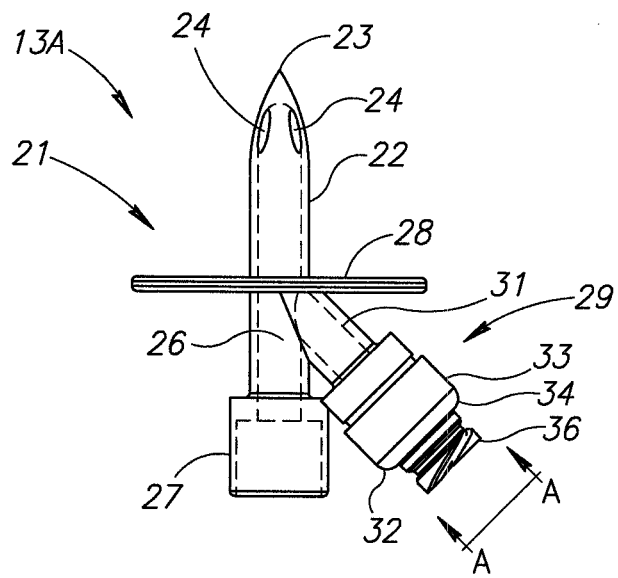
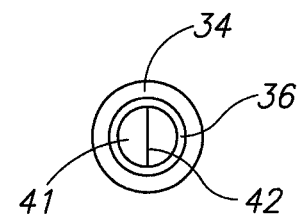
FIG.2A
FIG.2B
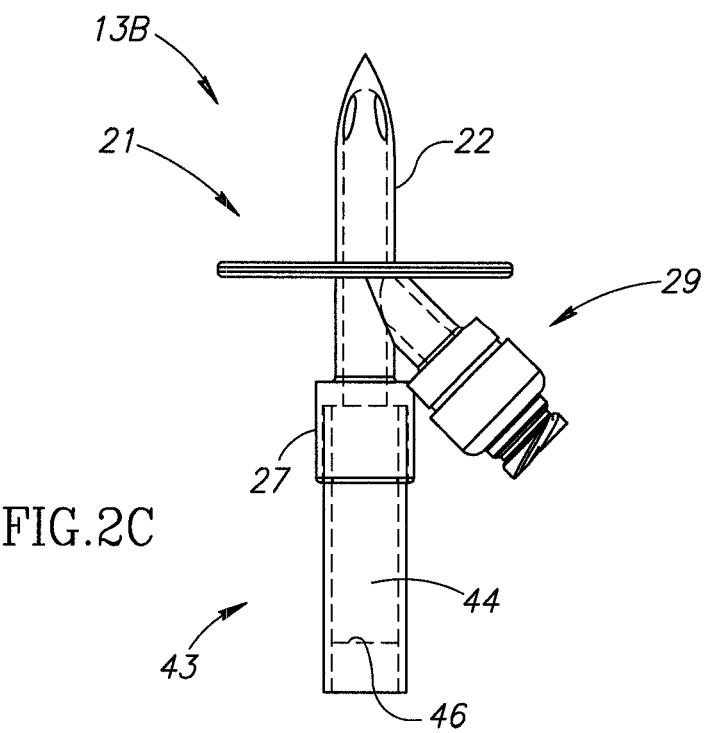
FIG.2C

NEEDLELESS ADDITIVE CONTROL VALVE

CROSS-REFERENCE TO RELATED APPLICATIONS

This application is a continuation-in-part of International Patent Application No. PCT/IL2006/001228, filed Oct. 26, 2006, which was published in the English language on May 10, 2007, under International Publication No. WO 2007/052252 A1 and the disclosure of which is incorporated herein by reference.

BACKGROUND OF THE INVENTION

The invention pertains to additive control valves for use with fluid containers containing an infusion liquid and an intravenous (IV) or administration port for administrating the infusion liquid.

Conventional infusion bags having an intravenous (IV) or administration port for interconnection with an infusion set, a drip chamber, and a spike, and a self-sealing additive port for enabling needle injection of a liquid additive. However, needle injection into an infusion bag's additive port can inadvertently mix scrapings from its additive port with its infusion contents. Moreover, some needles have shrouds to avoid needle sticks but which preclude insertion into an additive port thus limiting certain shrouded needles to be used with infusion bags having specific additive ports thereby complicating the administration of medication to patients.

U.S. Pat. No. 4,581,014 to Millerd et al. illustrates and describes a fluid infusion system enabling interruption of a primary infusion fluid to a patient to permit administration of a secondary infusion fluid followed by resumption of primary fluid flow. The fluid infusion system includes a selector valve (12) with an upstanding primary spike (36) for puncturing an IV port (25) of an infusion bag, a generally upstanding dual path secondary spike (44) for puncturing a vial's self-sealing rubber stopper, and an outlet fitting (54) for connection to the upper end of a drop chamber.

U.S. Pat. No. 5,647,845 to Haber et al. illustrates and describes a universal intravenous infusion system enabling mixing of a customized or generic fluid or powder medication with the fluid contents of an infusion bag so that the mixture can be administered according to the needs of a patient. The intravenous infusion system includes a fluid control valve (2) with an administration port cannula (14), a vial receiving and docking receptacle (20), and an IV drip chamber tube (18) with a fluid port (19) for mating to a conventional IV fluid line.

BRIEF SUMMARY OF THE INVENTION

The present invention is directed towards a needleless additive control valve for use with a fluid container containing an infusion liquid and an additive transfer device containing a liquid additive for either mixing the liquid additive with the infusion liquid or direct administration to a patient. The needleless additive control valve has a trifurcate connector body including an IV spike for sealing insertion into a fluid container's IV or administration port, an outlet port, and a normally closed (NC) needleless additive port for selective fluid connection with an additive transfer device wherein the IV spike, the outlet port and the NC needleless additive port are in 3 way direct and continuous fluid communication. Various types of connectors, tubing, and the like, can be inserted into the outlet port. Alternatively, the outlet port can be optionally fitted with a substitute IV port for sealingly receiving an IV spike. The needleless additive control valve of the present invention affords a simple low cost device for use with conventional additive transfer devices with male connectors and enabling access to a fluid container by way of an IV infusion set, a drip chamber, a spike, and the like. The male connectors are preferably male Luer connectors of either the slip type or the lock type.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 2A is a front view of a needleless additive control valve with a self-sealing access valve;

FIG. 2B is a front view of the self-sealing access valve;

FIG. 2C is a front view of the needleless additive control valve fitted with a substitute IV port;

DETAILED DESCRIPTION OF THE INVENTION

Figure 1:
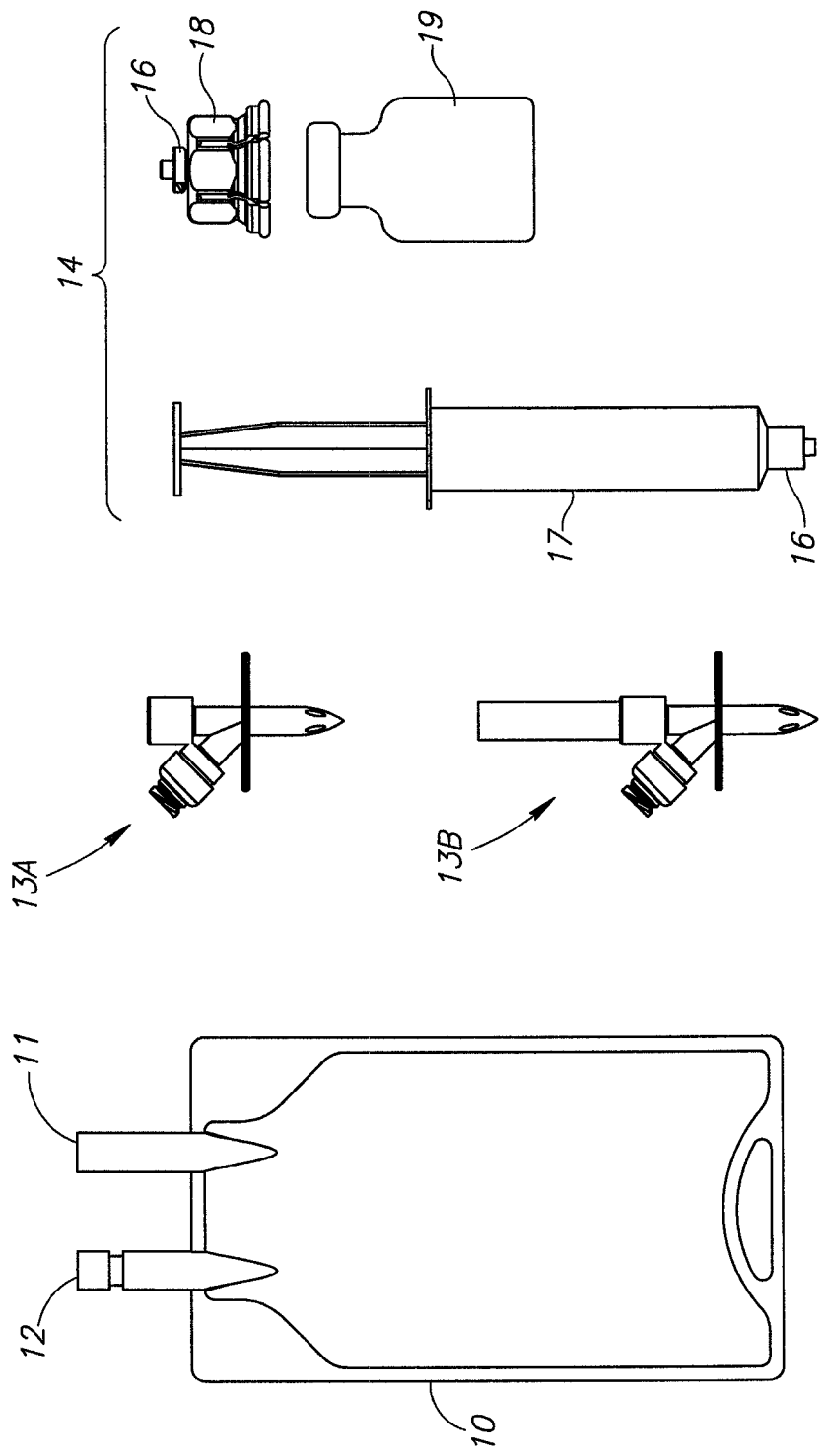
FIG. 1 is a pictorial view of an infusion bag, needleless additive control valves, a syringe, a vial adapter, and a vial.

FIG. 1 shows a conventional infusion bag 10 containing an infusion liquid and having an intravenous (IV) or administration port 11 and an additive port 12, needleless additive control valves 13A and 13B, and an additive transfer device 14 having a male Luer lock connector 16. The additive transfer device 14 can be constituted by a syringe 17, a vial adapter 18 for snap fit telescopic mounting onto a vial 19, and the like. Suitable vial adapters 18 with integrally formed puncturing members for puncturing a vial's rubber stopper are commercially available from Medimop Medical Projects Ltd., Ra'anana, Israel (www.medimop.com). The vial 19 can contain a liquid additive or a lyophilized powder drug requiring reconstitution with a diluent prior to administration.

FIG. 2A shows the needleless additive control valve 13A has a trifurcated connector body 21 including an IV spike 22 for sealing insertion into an IV port 11, an outlet port 27, and a needleless additive port 29 wherein the IV spike 22, the port 27 and the needleless additive port 29 are in 3 way direct and continuous fluid communication. The IV spike 22 includes a spiked end 23 with peripherally disposed apertures 24, a lumen 26 terminating in the outlet port 27, and a circular flange 28 for restricting insertion into the IV port 11. The connector body 21 is preferably formed as an injection molded monolithic structure from suitable rigid plastic material such as polycarbonate, and the like.

Figure 3A:
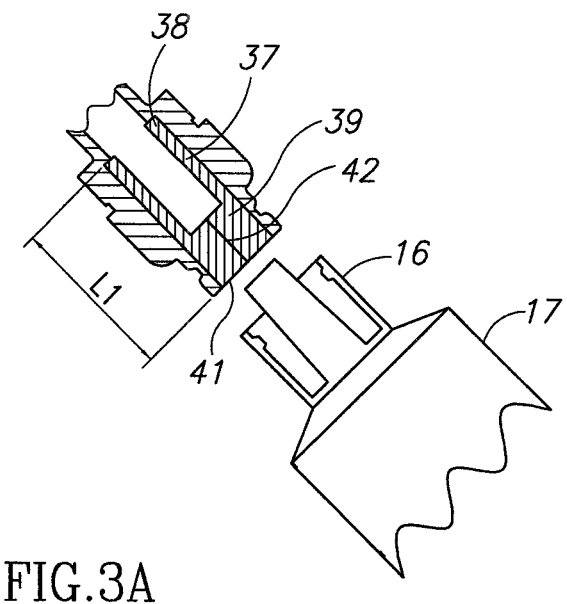
FIG. 3A is a cross section of the self-sealing access valve in its closed condition along line A-A in FIG. 2A.
Figure 3B:
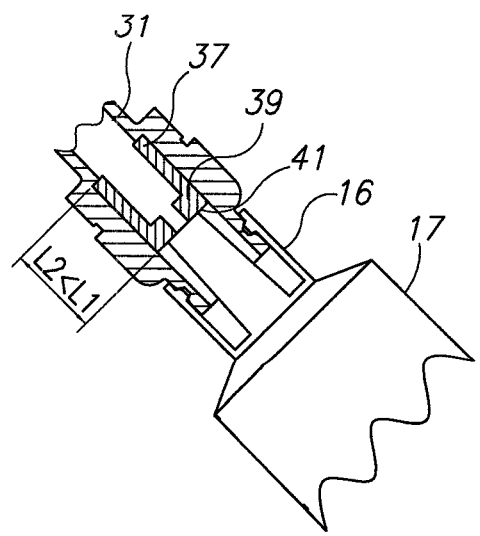
FIG. 3B is a cross section of the self-sealing access valve in its open condition along line A-A in FIG. 2A.

The needleless additive port 29 has a lumen 31 and is fitted with a self-sealing access valve 32 for screw threadingly receiving a male Luer lock connector 16. The access valve 32 is typically formed from rigid transparent plastic material such as polycarbonate, and the like. The access valve 32 has a stepped exterior surface 33 including an abutment surface 34 and a rim 36. The access valve 32 houses a silicone self-sealing valve member 37 with a tubular main portion 38 and a cylindrical needleless entry portion 39. The needleless entry portion 39 has an exposed entry surface 41 and a pre-formed slit 42 extending therealong. The valve member 37 has a natural length L1 and is so dimensioned that the entry surface 41 is flush with the rim 36 thereby enabling the entry surface 41 to be readily swabbed for sterilization purposes (see FIG. 3A). A male Luer connector 16 screw threaded onto the access valve 32 advances until it abuts against the abutment surface 34. During its advancement, the male Luer connector 16 compresses the valve member 37 to a compressed length L2<L1 which parts the entry portion 39 along its pre-formed slit 42 for enabling fluid communication between an additive transfer device and the lumen 31 (see FIG. 3B).

FIG. 2C shows a needleless additive control valve 13B including an outlet port 27 pre-fitted with a substitute IV port 43 having a lumen 44 and a sealing membrane 46. The substitute IV port 43 is a conventional IV port made from suitable flexible plastic material, for example, PVC, and the like, for sealingly receiving an about 5 mm to 6 mm diameter IV spike (not shown).

Figure 4A:
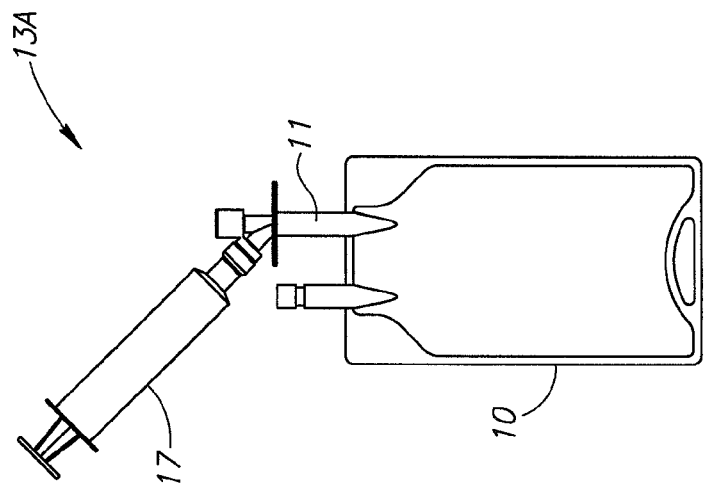
FIGS. 4A and 4B show the use of the needleless additive control valve with a syringe containing a liquid additive.
Figure 4B:
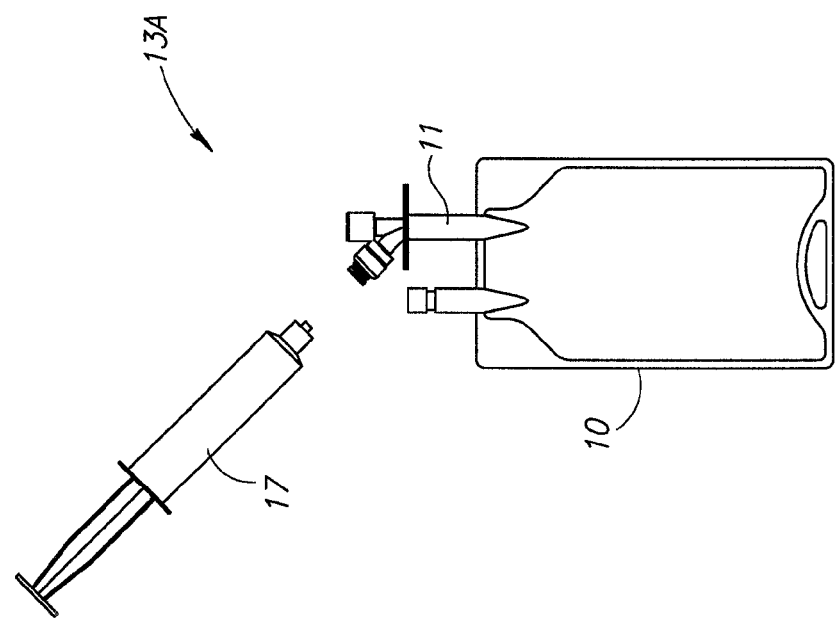

FIGS. 4A and 4B show the use of the needleless additive control valve 13A with an infusion bag 10 and a syringe 17. Various types of connectors, tubing, and the like, can be inserted into the outlet port 27. A syringe 17 can be pre-filled with a liquid additive. Alternatively, a syringe 17 can be filled with a liquid drug reconstituted from a lyophilized powder drug vial. A reconstituted liquid drug may have been reconstituted with liquid contents aspirated from an infusion bag. The syringe 17 can be employed for injecting a liquid additive into the infusion bag 10 prior to administration of infusion liquid to a patient. Alternatively, the syringe 17 can be employed for administrating a liquid additive to a patient during an infusion procedure.

Figure 5A:
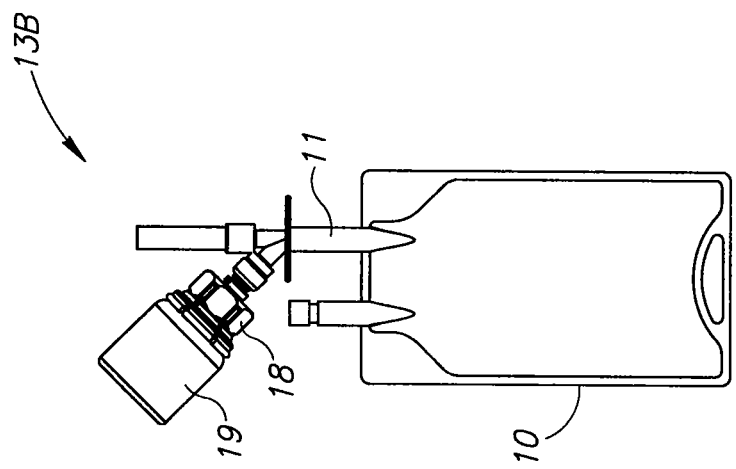
FIGS. 5A and 5B show the use of the needleless additive control valve fitted a substitute IV port with a vial adapter mounted on a vial containing a liquid additive.
Figure 5B:
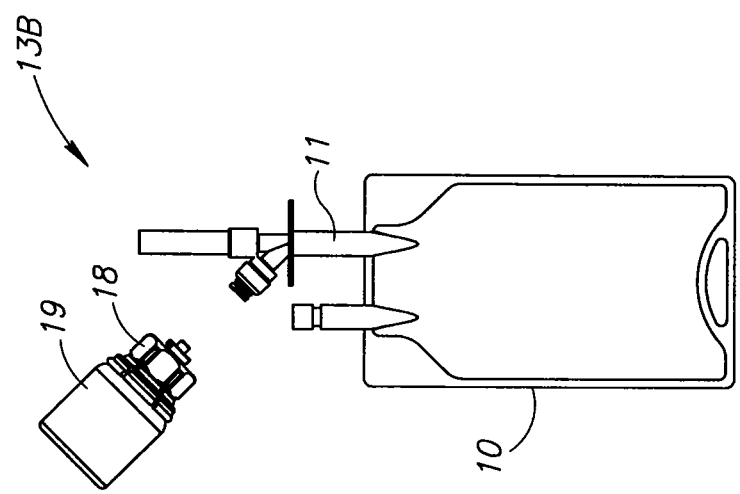

FIGS. 5A and 5B show the use of the needleless additive control valve 13B with an infusion bag 10 and a vial adapter 18 mounted on a vial 19. In the case that the vial 19 contains a liquid additive, the contents of the vial 19 can be mixed with an infusion liquid prior to administration of infusion liquid to a patient or administered to a patient during an infusion procedure. In the case that the vial 19 contains a lyophilized powder drug, the drug can be reconstituted by squeezing on the infusion bag 10 for forcing liquid from the infusion bag 10 into the vial 19. The reconstitution of the entire contents of a vial 19 may require several flushes with diluent.

While the invention has been described with respect to a limited number of embodiments, it will be appreciated that many variations, modifications, and other applications of the invention can be made within the scope of the appended claims. For example, the self-sealing access valve can be replaced by a manually operated stop cock, and the like.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A needleless additive control valve for use with a fluid container containing an infusion liquid and having an intravenous (IV) port for administrating the infusion liquid, the needleless additive control valve comprising a trifurcated connector body having an IV spike with a spiked end for sealing insertion into the IV port, an outlet port fitted with a substitute IV port having a sealing membrane and being configured to sealingly receive a second IV spike for connection to an administration line, the sealing membrane being opened by insertion of the second IV spike into the substitute IV port, and a needleless additive port with a female connector alternately sealingly receiving a male connector of both a needleless syringe containing a liquid additive and a vial adapter connected to a vial containing a medicament additive, the needleless additive port being configured to receive a screw threaded male connector and including (i) an exposed needleless access surface capable of being sterilized for multiple sterile sealing insertions of the male connector therethrough and (ii) a self-sealing access valve urged from a normally closed condition to an open condition on a sealing insertion of a male connector therein;

a first lumen extends between the IV spike and the outlet port within the connector body; and a second lumen extends from the needleless additive port and intersects with the first lumen within the connector body to be in fluid communication therewith such that said IV spike, said outlet port and said needleless additive port are in 3 way direct and continuous bi-directional fluid communication, thereby enabling the liquid additive of the needleless syringe and/or the medicament additive of the vial to be either mixed with the infusion liquid or directly administered to a patient.

* * * * *